(12) United States Patent
Wan et al.

(10) Patent No.: US 7,205,109 B2
(45) Date of Patent: Apr. 17, 2007

(54) METHOD FOR DETECTING HEPATOCARCINOMA SUSCEPTIBILITY BY DETECTING A TUMOR RELATED GENE IN THE REGION OF HUMAN CHROMOSOME 17 P. 13. 3

(75) Inventors: Dafang Wan, Shanghai (CN); Jianren Gu, Shanghai (CN)

(73) Assignee: Shanghai Cancer Institute, Shanghai (CN)

( * ) Notice: Subject to any disclaimer, the term of this patent is extended or adjusted under 35 U.S.C. 154(b) by 123 days.

(21) Appl. No.: 10/498,584

(22) PCT Filed: Mar. 21, 2002

(86) PCT No.: PCT/CN02/00182

§ 371 (c)(1),
(2), (4) Date: Jun. 10, 2004

(87) PCT Pub. No.: WO03/050279

PCT Pub. Date: Jun. 19, 2003

(65) Prior Publication Data

US 2005/0042616 A1 Feb. 24, 2005

(30) Foreign Application Priority Data

Dec. 12, 2001 (CN) .................... 01 1 42628

(51) Int. Cl.
*C12Q 1/68* (2006.01)
*C07H 21/02* (2006.01)
*C07H 21/04* (2006.01)
*G01N 33/574* (2006.01)

(52) U.S. Cl. .................. 435/6; 435/7.1; 536/23.5; 536/24.31

(58) Field of Classification Search .............. None
See application file for complete search history.

(56) References Cited

U.S. PATENT DOCUMENTS 5,976,790 A 11/1999 Pinkel et al.

FOREIGN PATENT DOCUMENTS

CN 1281899 1/2001

OTHER PUBLICATIONS

Gu et al. GenBank Accession No. AF177341, May 21, 2001.*

\* cited by examiner

*Primary Examiner*—Carla J. Myers
(74) *Attorney, Agent, or Firm*—Dorsey & Whitney LLP

(57) ABSTRACT

The invention provides a method for diagnosing susceptibility of individual cancer (e.g. liver cancer), comprising the steps of detecting individual HC56 gene, transcript and/or protein, and comparing it with normal HC56 gene, transcript and/or protein. The difference show the possibility of individual cancer is higher than that in the normal population. The invention also provides the corresponding detection kit.

2 Claims, 3 Drawing Sheets

METHOD FOR DETECTING HEPATOCARCINOMA SUSCEPTIBILITY BY DETECTING A TUMOR RELATED GENE IN THE REGION OF HUMAN CHROMOSOME 17 P. 13. 3

FIELD OF INVENTION

This invention relates to the human tumor related gene HC56 in the region of sub-band 3 of band 3 of zone 1 of human chromosome 17 (17p13.3) and its uses. In particular, it relates to the method and kit for detecting tumor susceptibility based on the single nucleotide polymorphism or SNP of HC56.

PRIOR ART

The mortality rate of malignant tumor is just lower than that of cardio-and cerebro-vascular disease in China. The mortality rate of hepatocarcinoma is the third in common tumors, just below lung cancer and gastric cancer. The diagnostic and therapeutic means are lacking for hepatocarcinoma, except for microhepatocarcinoma. The development of carcinoma is a complex process involving multiple genes and steps and effected by the activation of many oncogenes and inactivation of anti-oncogenes. The anti-oncogenes are much important. Therefore, to find anti-oncogenes is one of the focuses of the current studies. The loss of heterozygosity (LOH) of a gene may result in the loss of normal characters. Anti-oncogenes may exist in the site having high frequency of LOH.

The key state laboratory in Shanghai Cancer Institute has studied human hepatocarcinoma gene for long time. In 1991, it was found that the development of hepatocarcinoma was related to the inactivation of p53, which had codon mutations not only on position 249 but also on other positions. (Li D. Z; Gu JR et al. Carcinogenesis 14 (2): 169, 1993). P53 is located in chromosome 17p13.1.

The researches on 17p13.3 have been reported overseas. Nishida et al. selected 10 polymorphism probes on 17p and studied the relationship between the LOH on 17p of human hepatocarcinoma and p53 mutation (Noashi Nishida et al., Cancer Research 53: 368–372, 1993). He deemed that the development of hepatocarcinoma might be related to unknown anti-oncogenes on 17p13.3. Schultz et al. (David C. Schultz, et al., Cancer Research 56: 1997–2002, 1996) proved that two new genes, OVCA1 and OVCA2, were located on 17p13.3 by allele deletion mapping and site-directed cloning. These two genes were expressed in normal epithelial cells of ovary, but were low-expressed or not expressed in oophoroma or ovary cancer cell lines. Wales et al. (Michele M. Wales et al., Nature Medicine: 570–577, 1995) discovered a candidate gene Hic-1 on 17p13.3 by analyzing the DNA methylation degree in tumor tissues, which was a transcription factor having a zinc-finger structure and was expressed widely in normal tissues but low-expressed in tumor cells.

However, the previous reports did not indicate the minimum range of LOH in hepatocarcinoma tissue and the corresponding sites. Further, the relationship between the above candidate genes and hepatocarcinoma was not reported.

Since cancer is one of the main diseases harmful to human health, people are concerned about the early diagnosis and gene therapy of cancer so as to effectively cure and prevent tumors, such as hepatocarcinoma. Therefore, there is a keen need in the art to develop new tumor-related and/or tumor-inhibiting human proteins and the corresponding detection kits.

SUMMARY OF INVENTION

One purpose of the invention is to provide a novel hepatoma related protein, named HC56 protein, and its fragments, analogs and derivatives.

Another purpose of the invention is to provide a polynucleotide encoding the polypeptides.

Still another purpose of the invention is to provide a method for HC56-based method and detection kit for detecting tumor susceptibility.

In the first aspect, the invention provides an isolated normal human HC56 polypeptide, which comprises the amino acid sequence of SEQ ID NO: 4. Further, it provides the amino acid mutation caused by SNPs when compared with the normal human HC56. One example of the mutated HC56 amino acid sequence is shown in SEQ ID NO: 2.

In the second aspect, the invention provides an isolated polynucleotide encoding the normal HC56 polypeptide, e.g., SEQ ID NO: 3. It further provides the SNPs in human HC56 gene. One HC56 sequence having SNPs is shown in SEQ ID NO: 1.

In the third aspect, the invention provides a vector comprising the above polynucleotide and a host cell transformed with the vector or a host cell transformed with the polynucleotide.

In the fourth aspect, the invention provides a method for producing a polypeptide having the activity of HC56 protein, which comprises (a) culturing the above transformed host cell under the conditions suitable for the expression of protein; (b) isolating the polypeptides having the activity of HC56 protein from the culture.

In the fifth aspect, the invention provides nucleic acid molecules for detection, which consist of 20–4750 consecutive nucleotides of SEQ ID NO: 3 and having mutations selected from the group consisting of:

SEQ ID NO: 3, position 2004, C→T;
SEQ ID NO: 3, position 2080, A→G;
SEQ ID NO: 3, position 2655, G→C;
SEQ ID NO: 3, position 3043, G→C;
SEQ ID NO: 3, position 3085, A→T;
SEQ ID NO: 3, position 3358, G→A;
SEQ ID NO: 3, position 4092, A→G;
SEQ ID NO: 3, position 4404, T→C;
SEQ ID NO: 3, position 4564, C→G;
SEQ ID NO: 3, position 4602, G→A.

Alternatively, the nucleic acid molecule has sequence of SEQ ID NO: 1. These nucleic acid molecules can be used as probes, primers or antisense fragments.

In the sixth aspect, the invention provides a method for detecting the carcinomatous change or cancer susceptibility of hepatocytes, comprising the steps of: detecting whether there is any change of HC56 gene, transcript and/or protein in the hepatocyte of the subject when compared with the normal HC56 gene, transcript and/or protein, and the change indicating that the possibility of suffering cancer in the subject is higher than that in the normal population. Preferably, the change is nucleotide deletion, insertion or substitution.

In one preferred embodiment, the HC56 gene or transcript are detected and compared with the normal HC56 nucleotide sequence and the change is selected from the group consisting of:

SEQ ID NO: 3, position 2004, C→T;
SEQ ID NO: 3, position 2080, A→G;
SEQ ID NO: 3, position 2655, G→C;
SEQ ID NO: 3, position 3043, G→C;
SEQ ID NO: 3, position 3085, A→T;
SEQ ID NO: 3, position 3358, G→A;
SEQ ID NO: 3, position 4092, A→G;

SEQ ID NO: 3, position 4404, T→C;
SEQ ID NO: 3, position 4564, C→G;
SEQ ID NO: 3, position 4602, G→A.

More preferably, the change is selected from the group consisting of:
SEQ ID NO: 3, position 3043, G→C;
SEQ ID NO: 3, position 3085, A→T;
SEQ ID NO: 3, position 4404, T→C;
SEQ ID NO: 3, position 4602, G→A.

In one preferred embodiment, the HC56 protein is detected and compared with the normal HC56 amino acid sequence and the change is selected from the group consisting of:
SEQ ID NO: 4, position 222, Pro→Ser;
SEQ ID NO: 4, position 247, Gln→Arg;
SEQ ID NO: 4, position 439, Glu→Gln;
SEQ ID NO: 4, position 568, Gly→Ala;
SEQ ID NO: 4, position 582, Glu→Val;
SEQ ID NO: 4, position 673, Arg→Gln;
SEQ ID NO: 4, position 926, Asn→Asp;
SEQ ID NO: 4, position 1022, Gys→Arg.

More preferably, the change is selected from the group consisting of:
SEQ ID NO: 4, position 568, Gly→Ala;
SEQ ID NO: 4, position 582, Glu→Val;
SEQ ID NO: 4, position 1022, Gys→Arg.

In the seventh aspect, the invention provides a kit for detecting tumor (e.g., hepatocarcinoma) susceptibility, which comprises primers which specifically amplify human HC56 gene or transcript to produce an amplification product having a SNP selected from the group consisting of:
SEQ ID NO: 3, position 2004, C→T;
SEQ ID NO: 3, position 2080, A→G;
SEQ ID NO: 3, position 2655, G→C;
SEQ ID NO: 3, position 3043, G→C;
SEQ ID NO: 3, position 3085, A→T;
SEQ ID NO: 3, position 3358, G→A;
SEQ ID NO: 3, position 4092, A→G;
SEQ ID NO: 3, position 4404, T→C;
SEQ ID NO: 3, position 4564, C→G;
SEQ ID NO: 3, position 4602, G→A.

Preferably, the kit further comprises the probes specifically binding to the SNP site and/or a restriction enzyme specifically recognizing the SNP site wherein the nucleotide change in the SNP site results in the appearance or disappearance of the cleavage site of restriction enzyme. More preferably, the restriction enzyme is selected from SecI and EarI.

Preferably, the change is selected from the group consisting of:
SEQ ID NO: 3, position 3043, G→C;
SEQ ID NO: 3, position 3085, A→T;
SEQ ID NO: 3, position 4404, T→C;
SEQ ID NO: 3, position 4602, G→A.

The other aspects of the invention will be apparent to the skilled in the art in light of the technical disclosure of the invention.

DETAILED DESCRIPTION OF INVENTION

Figure 1:
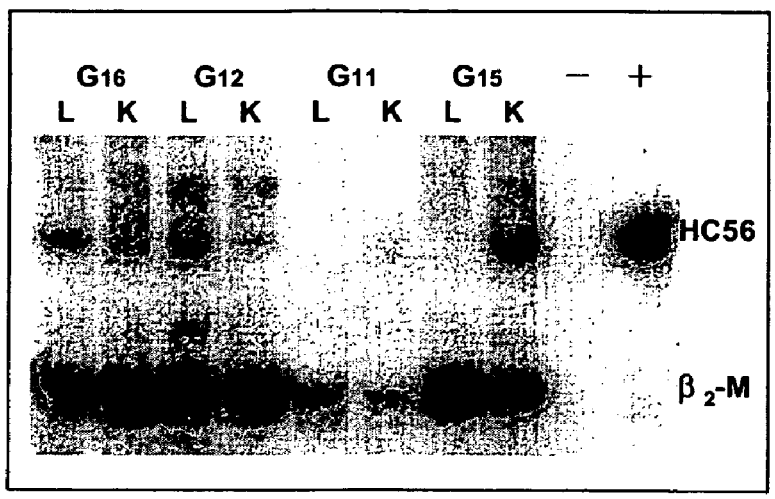
FIG. 1 and FIG. 2 show the expression of HC56 in hepatocarcinoma and surrounding noncancerous tissues (RT-PCR), wherein G2, G4, G11, G12, G15, G16, D1, D22, D24 were from hepatocarcinoma patients. L: noncancerous liver tissues; K: cancerous liver tissues; +: positive control; −: negative control; β2-M: β-microglobulin control probe.

In the hepatocarcinoma study, the inventors first found that there was high frequency of LOH (60–100%) of 17p13.3 in hepatocarcinoma (HC) tissue. Recently, the full genomic scanning of HC also proved that 17p13.3 was the region having the highest frequency. The inventors isolated and cloned the tumor related ESTs or expressed sequence tags in region 17p13.3 by screening the normal liver cDNA library using PAC P579 clone corresponding to site 926 in region 17p13.3. The cDNA clone was obtained. The full-length nucleotide sequence, named HC56, and the encoded amino acid sequence were obtained by RACE. The Northern blotting, RT-PCR and Southern blotting results proved that HC56 was related to tumor. The in vitro experiment proved that HC56 inhibited the growth of liver cancer cell line 7721. The study also indicated that there were several SNPs in the exon regions of HC56. Therefore, HC56 gene can be used in the diagnosis, treatment and prevention of tumor.

HC56 protein has various uses including, but not to be limited to: curing disorders (e.g., tumor) caused by low or no activity of HC56 protein, and screening out antibodies, polypeptides or ligands as agonists of HC56. The expressed recombinant HC56 protein can be used to screen polypeptide library to find out therapeutically valuable polypeptide molecules that activate HC56 protein.

In another aspect, the invention also provides the polyclonal and monoclonal antibodies, especially the monoclonal antibody, which are specifically against the polypeptide encoded by human HC56 DNA or fragments thereof. By "specificity", it is meant an antibody that binds to the HC56 gene products or fragments thereof. Preferably, the antibody specifically binds to the protein having an amino acid sequence of SEQ ID NO: 2 and does not bind to the protein having an amino acid sequence of SEQ ID NO: 4.

The present invention includes not only intact monoclonal or polyclonal antibodies, but also immunologically-active antibody fragments, e.g., a Fab' or (Fab)$_2$ fragment, an antibody light chain, an antibody heavy chain, a genetically engineered single chain Fv molecule, or a chimeric antibody.

The antibodies in the present invention can be prepared by various techniques known to those skilled in the art. For example, purified HC56 gene products, or its antigenic fragments can be administrated to animals to induce the production of polyclonal antibodies. Similarly, cells expressing HC56 or its antigenic fragments can be used to immunize animals to produce antibodies. Antibodies of the invention can be monoclonal antibodies that can be prepared by using hybridoma technique. The polyclonal antibodies can be prepared by immunizing animals, such as rabbit, mouse, and rat, with HC56 protein. Various adjuvants, e.g., Freund's adjuvant, can be used to enhance the immunization. The antibody against HC56 protein can be used in immunohistochemical method to detect the presence of HC56 protein in the biopsy specimen.

The invention further provides diagnostic assays for quantitative and in situ measurement of HC56 protein level. These assays are well known in the art and include FISH assay and radioimmunoassay. The level of HC56 protein detected in the assay can be used to illustrate the importance of HC56 protein in diseases and to determine the diseases associated with HC56 protein.

A method of detecting the presence of HC56 protein in a sample by utilizing the antibody specifically against HC56 protein comprises the steps of: contacting the sample with the antibody specifically against HC56 protein; observing the formation of antibody complex, which indicates the presence of HC56 protein in a sample.

The polynucleotide encoding HC56 protein can be used in the diagnosis of HC56 protein related diseases. The polynucleotide encoding HC56 can be used to detect whether HC56 is expressed or not, and whether the expression of HC56 is normal or abnormal, e.g., in the case of diseases. HC56 DNA sequences can be used in the hybridization with biopsy samples to determine the expression of HC56. The hybridization methods include Southern blotting, Northern blotting and in situ blotting, etc., which are public and sophisticated techniques. The corresponding kits are commercially available. A part of or all of the polynucleotides of the invention can be used as probe and fixed on a microarray or DNA chip for analysis the differential expression of genes in tissues and for the diagnosis of genes. The HC56 specific primers can be used in RNA-polymerase chain reaction and in vitro amplification to detect the transcripts of HC56.

Further, detection of the mutation of HC56 gene is useful for the diagnosis of HC56 protein related diseases. The mutation forms of HC56 include site mutation, translocation, deletion, rearrangement and any other mutations compared with the wild-type HC56 DNA sequence. The conventional methods, such as Southern blotting, DNA sequencing, PCR and in situ blotting, can be used to detect mutation. A preferred method for detecting the mutation of HC56 nucleic acid is to detect the presence of SNPs. Moreover, mutation sometimes affects the expression of protein. Therefore, Northern blotting and Western blotting can be used to indirectly determine whether the gene is mutated or not.

The invention also provides a kit for detecting the presence of SNPs of HC56 in the analyte, which comprises a suitable container, primers located in the container which specifically amplify HC56 gene or transcripts to produce an amplification products having the SNP sites identified in the invention, and the specification.

The invention has the following characterizations: it has been proved that the LOH or DNA rearrangement of HC56 exists in HC tissues by Southern blotting; it has been proved that the expression of HC56 is inhibited in certain HC tissues by Northern blotting. Therefore, it is suggested HC56 is related to the development of HC and is a candidate for HC anti-oncogene. The in vitro DNA transfection has shown that HC56 remarkably inhibits the growth of HC cells. The SNP detection has shown that at least two SNPs have sufficient statistical difference (p<0.01) between the HC patient peripheral blood DNA and normal peripheral blood DNA. Therefore, the SNP detection kit is useful for detecting HC susceptibility.

The invention is further illustrated by the following examples. It is appreciated that these examples are only intended to illustrate the invention, but not to limit the scope of the invention. For the experimental methods in the following examples, they are performed under routine conditions, e.g., those described by Sambrook. et al., in Molecule Clone: A Laboratory Manual, N.Y.: Cold Spring Harbor Laboratory Press, 1989, or as instructed by the manufacturers, unless otherwise specified.

EXAMPLE 1 cDNA Cloning of HC56

DNA was extracted from P579 (Genome System Co.) and cut with NotI. The DNA fragments about 100 bp were recovered and used as probes. After labeling with $^{32}$P-dATP, the probes were used to screen the human liver cDNA library conventionally constructed. After pre-hybridization and hybridization, the positive clones were obtained.

The sequencing of one terminal sequence (about 500 bp) of cDNA clones was carried out on ABI 337 DNA autosequencer using dideoxy chain termination method. After analysis, the sequencing of the other terminal was carried out for some clones, which were determined to be new genes, until the full-length sequences were obtained. One clone was named HC56, whose nucleotide and amino acid sequences were shown in SEQ ID NOs: 3 and 4. The full-length sequence was 4750 bp and the ORF was from position 1341 to 4484, encoding a protein having 1047 amino acids.

The homology comparison did not find any polypeptide or protein homologous to HC56.

EXAMPLE 2

Full Length Gene Preparation Using RT-PCR

The normal human liver tissue was taken, and the total RNA was extracted using Trizol™ agents (GIBCO. BRL) according to the specification, and mRNA was extracted using mRNA Purification Kit (Pharmacia). The reverse transcription was carried out at 42 degree using MMLV-RT-Superscript II (GIBCO BRL) to obtain liver cDNA. Based on SEQ ID NO:3, the HC56 specific primers were synthesized. The protocol was 97° C., 3 min, 1 cycle; 94° C. 30 sec, 60° C. 30 sec, 72° C. 1 min, 35 cycles; 72° C. 10 min, 1 cycles. The amplification product containing complete ORF sequence was obtained. The sequencing confirmed the sequence of the products was in accord with sequence of Example 1.

EXAMPLE 3

Construction of HC56 Recombinant Expression Vector

Figure 9:
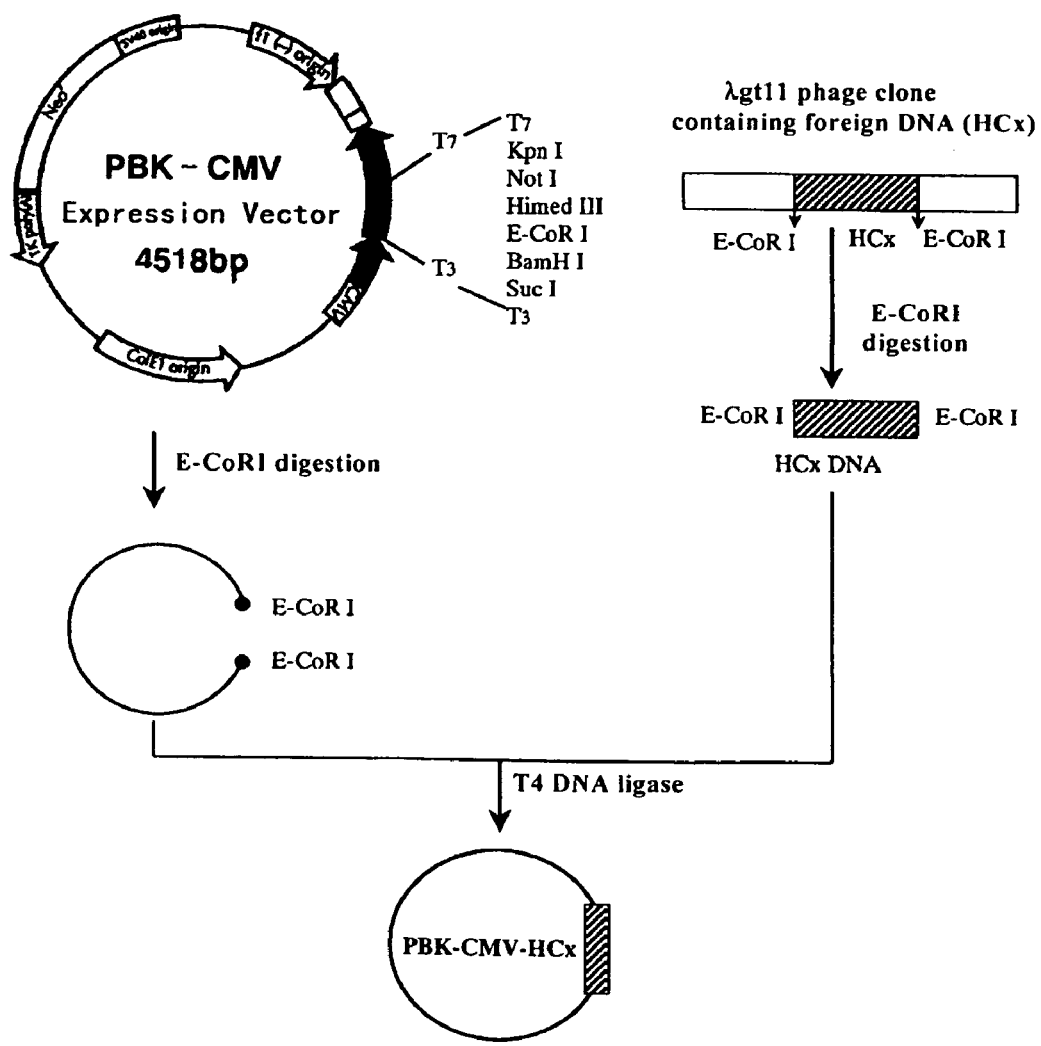
FIG. 9 shows the construction scheme of expression vector pBR-CMV-CHx.

DNA was extracted from HC56 clone prepared in Example 1. According to the scheme shown in FIG. 9, the extracted DNA was digested with EcoRI, ligated with pBK-CMV (Stratagene) digested with EcoRI, and transformed into susceptible cells of XLI-blue. The white clones were selected and plasmid DNA was prepared therefrom and confirmed by enzymatic digestion. The resultant recombinant expression vector pBK-CMV-HC56 was obtained.

EXAMPLE 4

Semi-Quantitative RT-PCR of HC56

1 μl of total tissue RNA was taken. In a 20 μl reaction system, the Superscript II RT kit (GIBCO. BRL) was used to synthesize the first strand of cDNA. Then, the following primers were used in PCR:

HC56 upstream primer: 5'-ctgcccacca ccatctgcca-3' (SEQ ID NO: 5)

Figure 2:
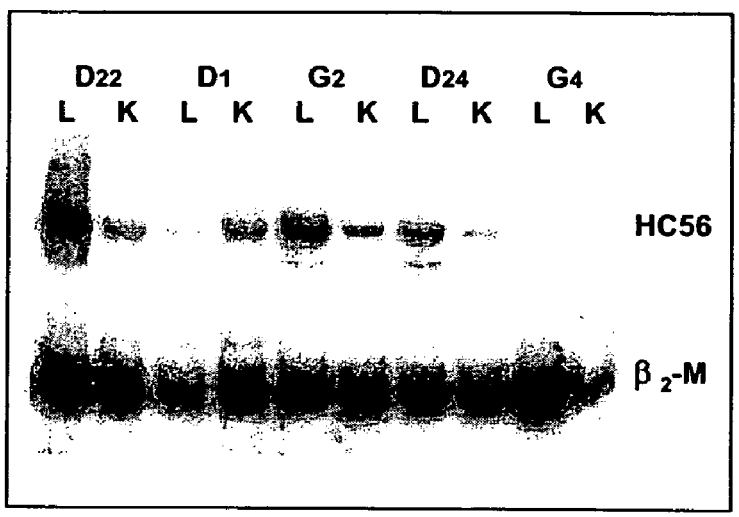

HC56 downstream primer: 5'-agcagcatgg ccaacagggg-3' (SEQ ID NO: 6).

β2-M was used as internal control DNA. After reaction, 3 μl PCR product was taken and run on 6% PAGE. The results were shown in FIGS. 1 and 2. Compared with β2-M, the expression bands of HC56 in L were much higher than those in K in Cases G2, G12, D24, were higher than those in K in Case G15, and were not different in other cases. It indicated that the expression of HC56 was inhibited in certain HC tissues.

EXAMPLE 5

Northern Blotting of HC56 Gene with Multi-Tissue Membrane

The multi-tissue Northern hybridization membrane (MTN) commercially available from Clontech was pre-hybridized at 42° C. for 3–4 hrs (Pre-hybridization solution contained 50% formamide, 0.05M Tris, 1% SDS, 5× Denhardt's solution, 0.1% sodium pyrophosphate, 100 mg/ml denatured sperm DNA), hybridized with HC56 probes, and shown by X-ray autoradiography.

Figure 3:
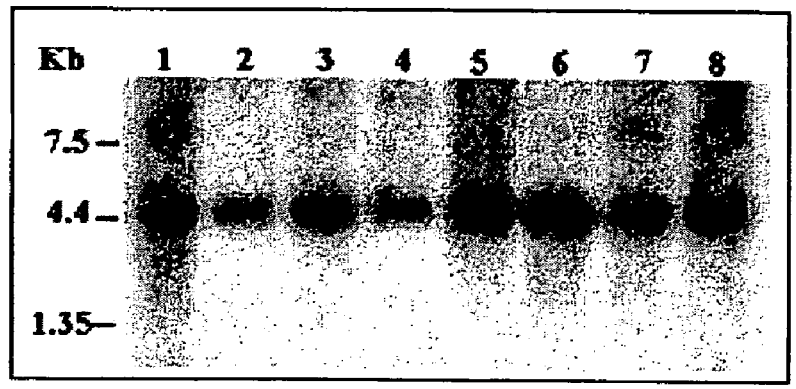
FIG. 3 shows the expression of HC56 in normal human tissues. Lanes 1–8 were heart, liver, brain, skeletal muscle, placenta, kidney, lung and pancreas, respectively.

The results were shown in FIG. 3, indicating HC56 was highly expressed in heart, placenta and skeletal muscle, low expressed in lung, and expressed in other tissues.

EXAMPLE 6

Southern Blotting of HC56

10 μg DNA extracted from human HC tissues and surrounding noncancerous tissues was completely digested by EcoRI and prepared into Southern membrane according to the method described in "Molecule Clone: A Laboratory Manual". The membrane was conventionally pre-hybridized, hybridized, and washed.

Figure 4:
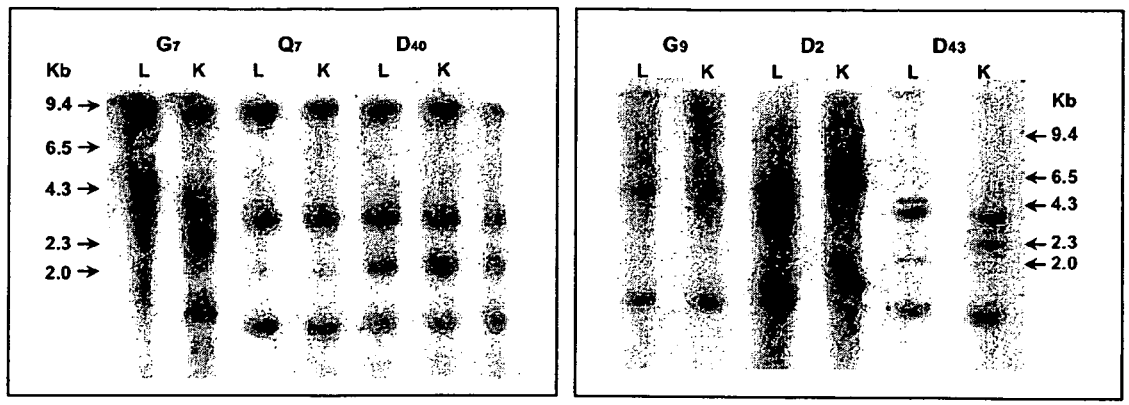
FIG. 4 shows the Southern blotting of HC56 wherein the genomic DNA was digested by MSPI. G7, Q7, D40, G9, D2, D43 were from hepatocarcinoma patients. L: noncancerous liver tissues; K: cancerous liver tissues.

As shown in FIG. 4, the positions of HC56 in the HC tissue (K) and noncancerous tissue (L) were different in Cases G7, D2, and D43, indicating DNA rearrangement in HC tissues.

Figures 5, 6:
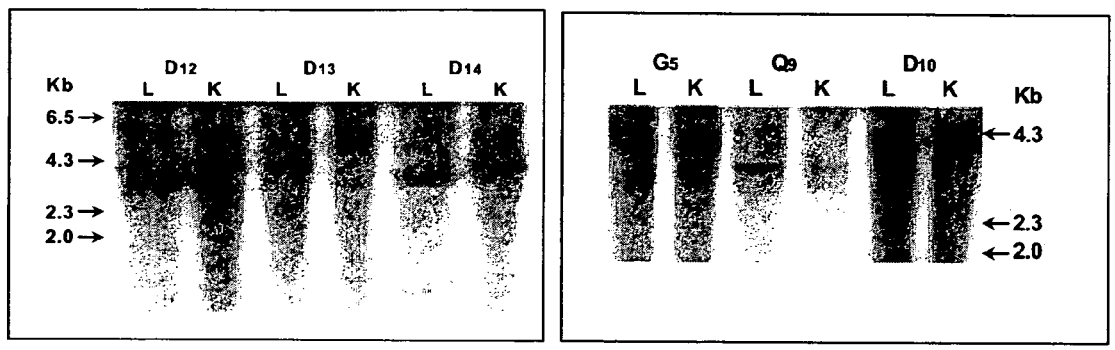
FIG. 5 shows the Southern blotting of HC56 wherein the genomic DNA was digested with EcoRI. D12, D13, D14 were from hepatocarcinoma patients. L: noncancerous liver tissues; K: cancerous liver tissues.
FIG. 6 shows the Southern blotting of HC56 wherein the genomic DNA was digested with EcoRI. G5, Q9, D10 were from hepatocarcinoma patients. L: noncancerous liver tissues; K: cancerous liver tissues.

As shown in FIGS. 5 and 6, there was one band of HC56 in the noncancerous tissues (L), but no band in the HC tissues (K) in Cases D13 and Q9, indicating DNA deletion.

TABLE 1

LOH or DNA rearrangement of HC56 in HC tissues

| cDNA clone | Sample (pairs) | LOH in HC | DNA rearrangement in HC | No difference between HC and noncancerous tissue |
|---|---|---|---|---|
| HC56 | 15 | 2 ($D_{13}$, $Q_9$) | 4 ($G_7$, $D_2$, $D_{43}$, $G_6$) | 9 |

*D12, G7 and so on were case numbers.

EXAMPLE 7

In Vitro Transforming HC56 cDNA into Hepatocarcinoma Cell

In this example, the liposome kit was used to in vitro transform hepatocarcinoma cell.

(1) Cell line: primary hepatocellular carcinoma cell line 7721

(2) DNA: DNA from expression plasmid pBK-CMV-HC56

(3) Liposome: LIPOFECT AMINE™ Reagent Kit (BRL Co.)

(4) Medium: non-serum medium SF-DMEM

Full-nutrient medium (supplemented with 10% FBS)

Full-nutrient medium containing G418

T25 culture flask.

(5) Preparation of DNA-liposome complex: 50 μl lipofectin was mixed with 50 μl SF-DMEM. DNA (20 μg, in 20 μl TE) was added into 80 μl SF-DMEM, and mixed. The diluted DNA was added into diluted lipofectin solution, mixed for 5–10 mins at room temperature. 1.3 ml SF-DMEM was added into DNA-lipofectin complex and the final volume was 1.5 ml.

(6) Transfecting cells: It was preferred that cells were grown to 80–90% confluence. Before experiment, the culture medium was changed once. 1.5 ml lipofectin-DNA complex was added onto the cell surface, gently shaken and mixed homogeneously, incubated at 37° C. for 1–3 hrs. 1.5 ml SF-DMEM was added and mixed homogeneously, and cells were incubated at 37° C. for 1–3 hrs. The culture medium was changed and cells were incubated at 37° C. overnight. When the confluence of cell was 70%, the medium was changed by the medium containing G418. Then the medium was changed as before until clones appeared.

Figure 7:
FIG. 7 shows cell line 7721 transfected by vector PBK-CMV.
Figure 8:
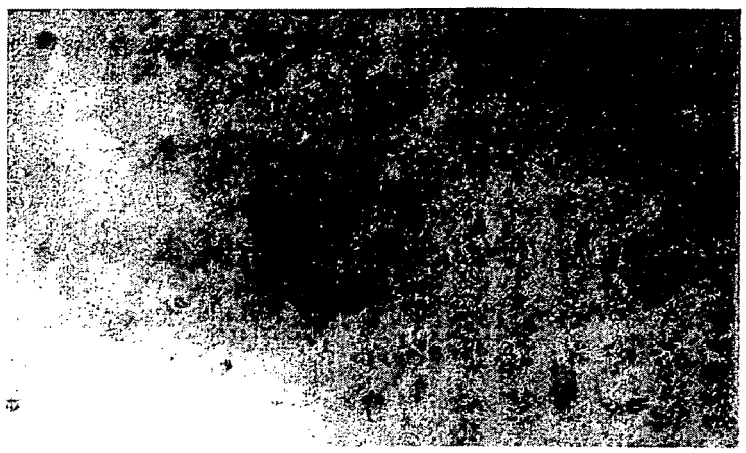
FIG. 8 shows cell line 7721 transfected by vector PBK-CMV-HC56.

The results were shown in FIGS. 7 and 8 and Table 2. In FIG. 7, the 7721 cells transfected by blank expression vector (pBK-CMV) formed many clones, while in FIG. 8, the 7721 cells transfected by expression vector containing HC gene formed no or only few clones. It indicated that HC56 in vitro inhibited the growth of HC cells.

TABLE 2

In vitro inhibition of HC56 on the growth of HC cells

| cDNA clone | Blank vector pBK-CMV | Positive control p21 | HC56 |
|---|---|---|---|
| Clone numbers (mean) | 11 | 0 | 0.3 |

EXAMPLE 8

SNPs Detection

The nested PCR primers and sequencing primers were constructed by using ABI3948 oligo synthesizer.

DNA was prepared conventionally from HC tissues, surrounding noncancerous tissues, and peripheral blood from patients. Meanwhile, the DNA from normal peripheral blood was prepared as control. The reaction system having a total volume of 50 μl contained 50 ng genomic DNA. The PCR was conducted in standard condition. The sequencing was carried on ABI 377 plate gel using ABI big Dye Terminator Chemistry, or using ABI3700 capillary sequencer. The SNPs or mutations were collected by Sequence Navigator™.

80 pairs of HC tissues and the surrounding noncancerous tissues were analyzed for SNPs in the exons of HC56 gene. There were 13 SNPs in the exons, 8 of which was accompanied by amino acid changes. Further, once position 3085 had a SNP, it was sure 3043, 4404, and 4602 also had SNPs. The results were shown in Table 3.

TABLE 3

High Frequency of cSNP

| Nucleotide no | Amino acid no | Nucleotide alteration | Amino acid Alteration | Linkage |
|---|---|---|---|---|
| 2004 | 222 | C→T | Pro→Ser | |
| 2080 | 247 | A→G | Gln→Arg | |
| 2655 | 439 | G→C | Glu→Gln | |
| 3043 | 568 | G→C | Gly→Ala | + |
| 3085 | 582 | A→T | Glu→Val | ⊕ |
| 3358 | 673 | G→A | Arg→Gln | |
| 4092 | 926 | A→G | Asn→Asp | |
| 4404 | 1022 | T→C | Gys→Arg | + |
| 3'UTR | | | | |
| 4564 | | C→G | | |
| 4602 | | G→A | | + |

70 patients' peripheral blood DNA and 100 normal persons' peripheral blood DNA were detected for SNPs on positions 3043 and 3085. It was found that the frequencies of SNPs in HC patients' peripheral blood DNA were higher than those in the normal person and had sufficient statistical difference (p<0.01), indicating HC56 was a susceptibility gene for The results were shown in Table 4.

EXAMPLE 9

Detection Kit

The hepatocarcinoma susceptibility detection kit was prepared, which comprised a pair of primers amplifying the SNPs on positions 3043 and 3085.

Upstream primer: 5'-tgtggagggt tttcaggaag-3' (SEQ ID NO: 7) (corresponding to positions 2861–2880 in SEQ ID NO: 1)

Downstream primer: 5'-tggagccagt attcctctcg-3' (SEQ ID NO: 8) (corresponding to positions 3357–3376 in SEQ ID NO: 1).

Further, the kit comprised restriction enzymes SecI and EarI, which were useful for detect the SNPs on positions 3043 and 3085. For the SNP on position 3043, once G was changed into C, the product could not be digested with SecI while the unchanged amplification product could be digested with SecI. For the SNP on position 3085, once A was changed into T, the product could not be digested with EarI while the unchanged amplification product could be digested with EarI. Therefore, the kit could easily detect the SNPs on positions 3043 and 3085 by digesting the amplification products.

All the documents cited herein are incorporated into the invention as reference, as if each of them is individually incorporated. Further, it would be appreciated that, in the above teaching of the invention, the skilled in the art could make certain changes or modifications to the invention, and these equivalents would still be within the scope of the invention defined by the appended claims of the present application.

TABLE 4 cSNP in C-56 and HCC

| | | Normal | Hepatocellular Carcinoma | | |
|---|---|---|---|---|---|
| SNP | | PBC(a) (%) n = 100 | PBC(b) (%) n = 70 | Non-Cancerous Liver(%) n = 80 | HCC (%) n = 80 |
| 3043bp (368aa) | G→C (Gly→Ala) | | | | |
| | G/G | 70.0 | 41.4 (29) | 42.5 (34) | 45.0 (36) |
| | G/C | 26.0 | 50.0 (35) | 50.0 (40) | 42.5 (34) |
| | C/C | 4.0 | 8.6 (6) | 7.5 (6) | 12.5 (10) |
| | (a Vs b p = 0.001) | | | | |
| *3085bp (582aa) | A→T (Glu→Val) | | | | |
| | A/A | 95.0 | 80.0 (56) | 76.3 (61) | 78.7 (63) |
| | A/T | 5.0 | 18.6 (13) | 22.5 (18) | 18.8 (15) |
| | T/T | 0.0 | 1.4 (1) | 1.2 (1) | 2.5 (2) |
| | (a Vs b p = 0.008) | | | | |
| 4404bp (1022aa) | T→C (Cys→Arg) | | | | |
| | T/T | 57.0 | 40.0 (28) | 45.0 (36) | 43.7 (35) |
| | T/C | 36.0 | 51.4 (36) | 45.0 (36) | 41.3 (33) |
| | C/C | 7.0 | 8.3 (6) | 10.0 (8) | 15.0 (9) |
| 4602bp 3'UTR | G→A | | | | |
| | G/G | 75.0 | 77.1 (54) | 75.0 (60) | 75.0 (60) |
| | G/A | 22.0 | 21.4 (15) | 21.2 (17) | 17.5 (14) |
| | A/A | 3.0 | 1.42 (1) | 3.8 (3) | 7.5 (6) |

*3085 A→T alteration linked with 3043, 4404, 4602, polymorphism in liver & HCC.

What is claimed is:

1. A method for detecting hepatocarcinoma susceptibility in a human subject comprising the steps of:
    detecting whether there is any change of HC56 gene or transcript in the subject when compared with the normal HC56 gene or transcript and the change indicating that the possibility of cancer in the subject is higher than that in the normal population,
    wherein the change comprises G→C in position 3043 in SEQ ID NO:3; and
    determining the hepatocarcinoma susceptibility in said human subject based on the change of HC56 gene or transcript.

2. The method of claim 1 wherein the method further comprises the steps of:

detecting whether there is any change of HC56 protein in the subject when compared with the normal HC56 protein, and the change of HC56 protein is Gly→Ala at amino acid position 568 of SEQ ID NO: 4
    determining the hepatocarcinoma susceptibility in said human subject based on the change of HC56 protein.

* * * * *

SEQUENCE LISTING

<160> NUMBER OF SEQ ID NOS: 8

<210> SEQ ID NO 1
<211> LENGTH: 4750
<212> TYPE: DNA
<213> ORGANISM: Homo sapiens
<220> FEATURE:
<221> NAME/KEY: CDS
<222> LOCATION: (1341)..(4484)
<223> OTHER INFORMATION:

<400> SEQUENCE: 1

```
tggccgtgtg attgctctgt gcccattacc ctgtggccgt gtgactgctg ctgtgcccat      60 tacccctgtgg ccgtgtgatt gctgctgtgc ccattaccct gtggccgtgt gattgctctg    120
tgcccattat cctgtggccg tgtgattgct ctgtgcccat accctgtgg  ccgtgtgatt    180 gctctgtgcc cattaccctg tggccgtgtg attgctctgt gcccattatc ctgtggccgt     240
gtgattgctc tgtgcccatt atcctgtggc cgtgtgattg ctctgtgccc attatcctgt     300
ggccgtgtga ttgctctgtg cccattatcc tgtggccgtg tgattgctgc tgtgcccatt     360
accctgtggc cgtgtgattg ctctgtgccc attatcctgt ggccgtgtga ttgctctgtg     420
cccattatcc tgtggctgtg tgattgctct gtgcccatta cctgtagcc  gtgtgattgc     480 ttctgtgccc attaccctgt ggctgtgtga ttgctgctgt gcccattatc ctgtggctgt     540
gtgattgctg ctgtgcccat accctgtggg ctgtgtgatg ctctgtgccc attaccctgt     600
ggctgtgtga ttgctctgtc ccattatcct gtggccgtgt gattgctgct gtgcctgtta    660
ccctgtggct gtgtgattgc tctgtgccca ttaccctgtg gctatgctcc cttcatctgt     720
catgagaagc tcagctgtca tgtcctgtgg tacatgctca gtggcccctg tagtttgtac     780
tgtcctccta tttctaaacc cctctcccca catcctctgc tggcccagcc tttgctggag     840
ggtctcgcct cagcagccca gcttttttctt tcacacact  tttcctgaag atctcattc     900 accgtcttgg ttccggtgat ccctctgggc agatacctc  tcagaatcac atttcccagc     960
ttacttccct cctgaacttc cacctggcat ttccgttgct ggaggacatc tgtaccttga    1020
tggccaaagc tgaactcatc tttcctcaca cctgctctga ttctcctcca ttccctgtat    1080
gtgatgtcac ctggtggcct cccagttccc aggctggaga gctcggaagc cattctggat    1140
tcctcggcca agtccttctg actccagctg tgcagtggct cttgtagtca tccattctcc    1200
ccgtccgctg atgtccttta aaaccctgt  catctcaaac catgacagcc tactaacagc    1260
agtggccatc tggaaacatt ttcactatac tgtcttattt ggcttgtctg tgtgcaggac    1320
ccttgaacat ctgtgaagaa atg act att ctg cat gga ggc ttc ttg ctg gcc    1373
                     Met Thr Ile Leu His Gly Gly Phe Leu Leu Ala
                       1               5                  10 gag cag ctg ttc cac cct aag gca ctg gca gaa tta aca aag tct gac       1421
Glu Gln Leu Phe His Pro Lys Ala Leu Ala Glu Leu Thr Lys Ser Asp
        15                   20                  25 tgg gaa cgt gtt gga cgg ccc atc gtg gag gcc tta agg gag atc tcc      1469
Trp Glu Arg Val Gly Arg Pro Ile Val Glu Ala Leu Arg Glu Ile Ser
    30                  35                  40 tcg gct gca gca cac tcc cag ccc ttt gcc tgg aag aag aaa gcc ctg      1517
Ser Ala Ala Ala His Ser Gln Pro Phe Ala Trp Lys Lys Lys Ala Leu
45                  50                  55 atc atc atc tgg gcc aag gtt ctg cag ccg cac ccc gtg acc ccg tcc      1565
Ile Ile Ile Trp Ala Lys Val Leu Gln Pro His Pro Val Thr Pro Ser
60                  65                  70                  75
```

-continued

| | |
|---|---|
| gac aca gag aca cgg tgg cag gaa gac ctg ttc ttc tcg gtg ggc aac<br>Asp Thr Glu Thr Arg Trp Gln Glu Asp Leu Phe Phe Ser Val Gly Asn<br>                        80                                85                          90 | 1613 |
| atg atc ccc acc atc aac cac acc atc ctc ttc gag ctg ctc aaa tcc<br>Met Ile Pro Thr Ile Asn His Thr Ile Leu Phe Glu Leu Leu Lys Ser<br>                      95                                100                         105 | 1661 |
| ctg gaa gct tct gga ctc ttt atc cag ctc ctg atg gcc ctg ccc acc<br>Leu Glu Ala Ser Gly Leu Phe Ile Gln Leu Leu Met Ala Leu Pro Thr<br>                        110                              115                         120 | 1709 |
| acc atc tgc cat gca gaa cta gag cgc ttt ctg gaa cat gtg acc gtt<br>Thr Ile Cys His Ala Glu Leu Glu Arg Phe Leu Glu His Val Thr Val<br>125                          130                              135 | 1757 |
| gac act tct gcc gaa gac gtg gcc ttc ttc ctg gac gtc tgg tgg gag<br>Asp Thr Ser Ala Glu Asp Val Ala Phe Phe Leu Asp Val Trp Trp Glu<br>140                          145                              150                         155 | 1805 |
| gtg atg aag cac aag ggt cac ccg cag gac ccc ctc tcc cag ttt<br>Val Met Lys His Lys Gly His Pro Gln Asp Pro Leu Leu Ser Gln Phe<br>                        160                                165                         170 | 1853 |
| agt gca atg gcc cat aag tac ctg cct gcc tta gat gag ttc ccc cat<br>Ser Ala Met Ala His Lys Tyr Leu Pro Ala Leu Asp Glu Phe Pro His<br>               175                              180                         185 | 1901 |
| cct cca aag agg ctt agg tca gac cca gac gcg tgc ccc acc atg ccc<br>Pro Pro Lys Arg Leu Arg Ser Asp Pro Asp Ala Cys Pro Thr Met Pro<br>                        190                                195                         200 | 1949 |
| ctg ttg gcc atg ctg ctc cgc ggg ctg aca cag atc cag agt cgg atc<br>Leu Leu Ala Met Leu Leu Arg Gly Leu Thr Gln Ile Gln Ser Arg Ile<br>         205                                210                         215 | 1997 |
| ctg ggc ccg ggg agg aag tgc tgt gcg ctg gcc aac ctg gct gac atg<br>Leu Gly Pro Gly Arg Lys Cys Cys Ala Leu Ala Asn Leu Ala Asp Met<br>220                          225                              230                         235 | 2045 |
| ctg act gtg ttt gcg ctg aca gag gac gac ccc cag gag gtg tct gca<br>Leu Thr Val Phe Ala Leu Thr Glu Asp Asp Pro Gln Glu Val Ser Ala<br>                        240                                245                         250 | 2093 |
| acc gtg tat ctg gac aaa ctg gcc acg gtg atc tct gtg tgg aac tcg<br>Thr Val Tyr Leu Asp Lys Leu Ala Thr Val Ile Ser Val Trp Asn Ser<br>         255                                260                         265 | 2141 |
| gac acc cag aat ccc tac cac cag cag gcg ctg gca gag aag gtg aag<br>Asp Thr Gln Asn Pro Tyr His Gln Gln Ala Leu Ala Glu Lys Val Lys<br>270                          275                              280 | 2189 |
| gag gca gaa cgg gat gtc agc ctg acc tcg ctg gcc aaa ctc ccc agt<br>Glu Ala Glu Arg Asp Val Ser Leu Thr Ser Leu Ala Lys Leu Pro Ser<br>         285                                290                         295 | 2237 |
| gag acc att ttc gtg ggc tgc gag ttc ctg cac cac ctg ctg cgg gag<br>Glu Thr Ile Phe Val Gly Cys Glu Phe Leu His His Leu Leu Arg Glu<br>300                          305                              310                         315 | 2285 |
| tgg ggg gag gag ttg cag gcc gtg ctc cgc agc agc cag ggg aca agt<br>Trp Gly Glu Glu Leu Gln Ala Val Leu Arg Ser Ser Gln Gly Thr Ser<br>                        320                                325                         330 | 2333 |
| tac gac agc tac cgg ctg tgc gac agt ctg act tcc ttc agc cag aac<br>Tyr Asp Ser Tyr Arg Leu Cys Asp Ser Leu Thr Ser Phe Ser Gln Asn<br>         335                                340                         345 | 2381 |
| gcg acg ctc tac ctg aac cgc acc agc ctg tcc aag gag gac agg cag<br>Ala Thr Leu Tyr Leu Asn Arg Thr Ser Leu Ser Lys Glu Asp Arg Gln<br>350                          355                              360 | 2429 |
| gtg gtc tct gag ctg gcg gag tgt gtc agg gac ttc ctg agg aaa acg<br>Val Val Ser Glu Leu Ala Glu Cys Val Arg Asp Phe Leu Arg Lys Thr<br>         365                                370                         375 | 2477 |
| agc acg gtg ctg aag aac agg gcc ttg gag gat atc aca gct tcc att<br>Ser Thr Val Leu Lys Asn Arg Ala Leu Glu Asp Ile Thr Ala Ser Ile | 2525 |

-continued

```
            380                 385                 390                 395
gcc atg gcc gtc atc cag cag aag atg gac cgc cat atg gaa gtg tgc       2573
Ala Met Ala Val Ile Gln Gln Lys Met Asp Arg His Met Glu Val Cys
                    400                 405                 410 tac att ttt gcc tct gag aag aag tgg gcc ttc tcg gac gag tgg gta       2621
Tyr Ile Phe Ala Ser Glu Lys Lys Trp Ala Phe Ser Asp Glu Trp Val
                415                 420                 425 gcc tgc ctg ggg agt aac agg gcc ctc ttc cga gag cca gac ttg gtg       2669
Ala Cys Leu Gly Ser Asn Arg Ala Leu Phe Arg Glu Pro Asp Leu Val
            430                 435                 440 ttg agg ctg ctg gaa aca gtg ata gac gtc agc aca gct gac aga gcc       2717
Leu Arg Leu Leu Glu Thr Val Ile Asp Val Ser Thr Ala Asp Arg Ala
        445                 450                 455 atc cct gag tct cag atc cgg cag gtg atc cac ctg atc ctg gaa tgt       2765
Ile Pro Glu Ser Gln Ile Arg Gln Val Ile His Leu Ile Leu Glu Cys
    460                 465                 470                 475 tac gca gac ctc tcc ctg cca ggt aaa aat aaa gtc ctt gca ggt atc       2813
Tyr Ala Asp Leu Ser Leu Pro Gly Lys Asn Lys Val Leu Ala Gly Ile
                480                 485                 490 ctg cgt tcc tgg ggg cga aag ggc ctc tct gaa aag ttg ctg gct tat       2861
Leu Arg Ser Trp Gly Arg Lys Gly Leu Ser Glu Lys Leu Leu Ala Tyr
                495                 500                 505 gtg gag ggt ttt cag gaa gac ctc aat aca act ttt aac cag ctc act       2909
Val Glu Gly Phe Gln Glu Asp Leu Asn Thr Thr Phe Asn Gln Leu Thr
            510                 515                 520 cag agt gcc tcc gaa cag ggc ttg gca aaa gct gtg gcc tcc gtg gcc       2957
Gln Ser Ala Ser Glu Gln Gly Leu Ala Lys Ala Val Ala Ser Val Ala
        525                 530                 535 cgc ctg gtc ata gtg cac ccg gaa gtc acg gtg aag aaa atg tgc agc       3005
Arg Leu Val Ile Val His Pro Glu Val Thr Val Lys Lys Met Cys Ser
540                 545                 550                 555 ctg gct gtg gtc aat ctc ggc acc cac aag ttc ctg gcc cag att ctc       3053
Leu Ala Val Val Asn Leu Gly Thr His Lys Phe Leu Ala Gln Ile Leu
                560                 565                 570 act gcc ttc cct gcc ctt agg ttt gtg gaa gtg cag ggt ccc aat tca       3101
Thr Ala Phe Pro Ala Leu Arg Phe Val Glu Val Gln Gly Pro Asn Ser
            575                 580                 585 tct gcc act ttc atg gtg tca tgc ctc aaa gaa acc gtc tgg atg aag       3149
Ser Ala Thr Phe Met Val Ser Cys Leu Lys Glu Thr Val Trp Met Lys
        590                 595                 600 ttc tct aca ccc aag gaa gaa aag caa ttt tta gag ctc ctg aac tgc       3197
Phe Ser Thr Pro Lys Glu Glu Lys Gln Phe Leu Glu Leu Leu Asn Cys
    605                 610                 615 ctg atg agt ccc gtg aaa ccc caa ggg att cca gtg gct gct ctt ctt       3245
Leu Met Ser Pro Val Lys Pro Gln Gly Ile Pro Val Ala Ala Leu Leu
620                 625                 630                 635 gag cca gac gag gtg ctg aag gaa ttt gtc ctg cct ttc ttg agg tta       3293
Glu Pro Asp Glu Val Leu Lys Glu Phe Val Leu Pro Phe Leu Arg Leu
                640                 645                 650 gat gtt gaa gag gta gac ctc agt ctg agg atc ttc atc cag act cta       3341
Asp Val Glu Glu Val Asp Leu Ser Leu Arg Ile Phe Ile Gln Thr Leu
            655                 660                 665 gag gca aac gcg tgt cga gag gaa tac tgg ctc cag acc tgc tcc ccg       3389
Glu Ala Asn Ala Cys Arg Glu Glu Tyr Trp Leu Gln Thr Cys Ser Pro
        670                 675                 680 ttt cca ctc ctc ttc agc ttg tgc cag ctc ttg gac cgc ttc agc aaa       3437
Phe Pro Leu Leu Phe Ser Leu Cys Gln Leu Leu Asp Arg Phe Ser Lys
    685                 690                 695 tac tgg cag ctt ccc aag gag aag cgg tgc ctc tct ttg gat agg aag       3485
```

```
                Tyr Trp Gln Leu Pro Lys Glu Lys Arg Cys Leu Ser Leu Asp Arg Lys
                700                 705                 710                 715 gat cta gcg atc cat atc ctg gag ctc ctg tgt gag att gta tca gcc        3533
Asp Leu Ala Ile His Ile Leu Glu Leu Leu Cys Glu Ile Val Ser Ala
                    720                 725                 730 aat gct gag acc ttc tcc ccg gat gtc tgg atc aag tcc ctg tcc tgg        3581
Asn Ala Glu Thr Phe Ser Pro Asp Val Trp Ile Lys Ser Leu Ser Trp
                735                 740                 745 ctc cac cgc aag tta gaa cag cta gac tgg act gtg ggc ctg agg ctg        3629
Leu His Arg Lys Leu Glu Gln Leu Asp Trp Thr Val Gly Leu Arg Leu
            750                 755                 760 aag agc ttc ttc gag ggg cac ttc aag tgt gaa gtg cca gcc aca ctt        3677
Lys Ser Phe Phe Glu Gly His Phe Lys Cys Glu Val Pro Ala Thr Leu
        765                 770                 775 ttt gag atc tgt aag ctt tca gaa gac gag tgg acc tcc cag gcc cac        3725
Phe Glu Ile Cys Lys Leu Ser Glu Asp Glu Trp Thr Ser Gln Ala His
780                 785                 790                 795 cca ggg tac ggg gct ggc acg ggg ctc ctg gcc tgg atg gag tgc tgc        3773
Pro Gly Tyr Gly Ala Gly Thr Gly Leu Leu Ala Trp Met Glu Cys Cys
                    800                 805                 810 tgc gtc tcc agc ggc atc tcg gag agg atg ctg tct ctc ttg gtg gtg        3821
Cys Val Ser Ser Gly Ile Ser Glu Arg Met Leu Ser Leu Leu Val Val
                815                 820                 825 gac gtg ggc aat cct gag gag gtc aga ctg ttc agc aaa ggc ttt ctg        3869
Asp Val Gly Asn Pro Glu Glu Val Arg Leu Phe Ser Lys Gly Phe Leu
            830                 835                 840 gtg gcc ctg gtg caa gtc atg cct tgg tgc agc cct cag gag tgg cag        3917
Val Ala Leu Val Gln Val Met Pro Trp Cys Ser Pro Gln Glu Trp Gln
        845                 850                 855 cgc ctt cac cag ctg acc agg aga ctg ctg gag aag cag ctc ctc cat        3965
Arg Leu His Gln Leu Thr Arg Arg Leu Leu Glu Lys Gln Leu Leu His
860                 865                 870                 875 gtc cct tat agc ctg gaa tat att cag ttt gtt ccc ctg ctc aac ctg        4013
Val Pro Tyr Ser Leu Glu Tyr Ile Gln Phe Val Pro Leu Leu Asn Leu
                    880                 885                 890 aag ccc ttt gcc cag gag ttg caa ctc tcc gtc ctc ttc ctg agg act        4061
Lys Pro Phe Ala Gln Glu Leu Gln Leu Ser Val Leu Phe Leu Arg Thr
                895                 900                 905 ttc cag ttt ctc tgc agc cat agc tgt cgt aat tgg ctt cct ctg gaa        4109
Phe Gln Phe Leu Cys Ser His Ser Cys Arg Asn Trp Leu Pro Leu Glu
            910                 915                 920 ggc tgg aac cac gtg gtc aaa ctc ctc tgt ggc agt ctg acc cgc ctc        4157
Gly Trp Asn His Val Val Lys Leu Leu Cys Gly Ser Leu Thr Arg Leu
        925                 930                 935 ctg gac tca gtc agg gcg ata cag gca gct ggc cct tgg gtt caa gga        4205
Leu Asp Ser Val Arg Ala Ile Gln Ala Ala Gly Pro Trp Val Gln Gly
940                 945                 950                 955 cca gag cag gac ctg acc cag gaa gcc ctg ttt gtt tac acc cag gtg        4253
Pro Glu Gln Asp Leu Thr Gln Glu Ala Leu Phe Val Tyr Thr Gln Val
                    960                 965                 970 ttc tgc cat gct ctg cac atc atg gcc atg ctc cac ccg gag gtc tgt        4301
Phe Cys His Ala Leu His Ile Met Ala Met Leu His Pro Glu Val Cys
                975                 980                 985 gag cca ctc tac gtt tta gcc ttg gaa acc ctc acc tgc  tat gag act       4349
Glu Pro Leu Tyr Val Leu Ala Leu Glu Thr Leu Thr Cys  Tyr Glu Thr
            990                 995                 1000 ttg agc  aag acc aac cct tct  gtc agc tcc ttg ctc  cag agg gca        4394
Leu Ser  Lys Thr Asn Pro Ser  Val Ser Ser Leu Leu  Gln Arg Ala
    1005                1010                1015
```

-continued

| | | | | | | | | | | | | |
|---|---|---|---|---|---|---|---|---|---|---|---|---|
| cac | gag | cag | cgc | ttc | tta | aag | tcc | att | gct | gag | ggc | att | ggc | cct | 4439 |
| His | Glu | Gln | Arg | Phe | Leu | Lys | Ser | Ile | Ala | Glu | Gly | Ile | Gly | Pro | |
| | 1020 | | | | | 1025 | | | | | 1030 | | | | |
| gaa | gaa | cgg | cgc | caa | acc | ctg | ttg | cag | aag | atg | agc | agc | ttc | tga | 4484 |
| Glu | Glu | Arg | Arg | Gln | Thr | Leu | Leu | Gln | Lys | Met | Ser | Ser | Phe | | |
| 1035 | | | | | 1040 | | | | | 1045 | | | | | | cttggcgtgg ggagctgggc cccaacatgg cggtctgca aagatcagc agcttcttac 4544 ctgtgcggga gcgaaaaagc tgggcttcaa catggcaggt ctgtaggggt cagacccaag 4604 cagcctggac tttacagtta tgtgaaactg tccacaaaaa gtcatggcaa taatggtgta 4664 aagaaaatag tttcttgggt atttgtaacg tacaaactat cataaaaatt ctcctctttc 4724 ccaaaaaaaa aaaaaaaaaa aaaaaa 4750

<210> SEQ ID NO 2
<211> LENGTH: 1047
<212> TYPE: PRT
<213> ORGANISM: Homo sapiens

<400> SEQUENCE: 2

Met Thr Ile Leu His Gly Gly Phe Leu Leu Ala Glu Gln Leu Phe His
1               5                   10                  15

Pro Lys Ala Leu Ala Glu Leu Thr Lys Ser Asp Trp Glu Arg Val Gly
                20                  25                  30

Arg Pro Ile Val Glu Ala Leu Arg Glu Ile Ser Ser Ala Ala Ala His
            35                  40                  45

Ser Gln Pro Phe Ala Trp Lys Lys Ala Leu Ile Ile Ile Trp Ala
    50                  55                  60

Lys Val Leu Gln Pro His Pro Val Thr Pro Ser Asp Thr Glu Thr Arg
65                  70                  75                  80

Trp Gln Glu Asp Leu Phe Phe Ser Val Gly Asn Met Ile Pro Thr Ile
                85                  90                  95

Asn His Thr Ile Leu Phe Glu Leu Leu Lys Ser Leu Glu Ala Ser Gly
            100                 105                 110

Leu Phe Ile Gln Leu Leu Met Ala Leu Pro Thr Thr Ile Cys His Ala
        115                 120                 125

Glu Leu Glu Arg Phe Leu Glu His Val Thr Val Asp Thr Ser Ala Glu
    130                 135                 140

Asp Val Ala Phe Phe Leu Asp Val Trp Trp Glu Val Met Lys His Lys
145                 150                 155                 160

Gly His Pro Gln Asp Pro Leu Leu Ser Gln Phe Ser Ala Met Ala His
                165                 170                 175

Lys Tyr Leu Pro Ala Leu Asp Glu Phe Pro His Pro Lys Arg Leu
            180                 185                 190

Arg Ser Asp Pro Asp Ala Cys Pro Thr Met Pro Leu Leu Ala Met Leu
        195                 200                 205

Leu Arg Gly Leu Thr Gln Ile Gln Ser Arg Ile Leu Gly Pro Gly Arg
    210                 215                 220

Lys Cys Cys Ala Leu Ala Asn Leu Ala Asp Met Leu Thr Val Phe Ala
225                 230                 235                 240

Leu Thr Glu Asp Asp Pro Gln Glu Val Ser Ala Thr Tyr Leu Asp
                245                 250                 255

Lys Leu Ala Thr Val Ile Ser Val Trp Asn Ser Asp Thr Gln Asn Pro
            260                 265                 270

Tyr His Gln Gln Ala Leu Ala Glu Lys Val Lys Glu Ala Glu Arg Asp
        275                 280                 285

-continued

```
Val Ser Leu Thr Ser Leu Ala Lys Leu Pro Ser Glu Thr Ile Phe Val
    290                 295                 300

Gly Cys Glu Phe Leu His His Leu Leu Arg Glu Trp Gly Glu Leu
305                 310                 315                 320

Gln Ala Val Leu Arg Ser Ser Gln Gly Thr Ser Tyr Asp Ser Tyr Arg
                325                 330                 335

Leu Cys Asp Ser Leu Thr Ser Phe Ser Gln Asn Ala Thr Leu Tyr Leu
                340                 345                 350

Asn Arg Thr Ser Leu Ser Lys Glu Asp Arg Gln Val Val Ser Glu Leu
            355                 360                 365

Ala Glu Cys Val Arg Asp Phe Leu Arg Lys Thr Ser Thr Val Leu Lys
370                 375                 380

Asn Arg Ala Leu Glu Asp Ile Thr Ala Ser Ile Ala Met Ala Val Ile
385                 390                 395                 400

Gln Gln Lys Met Asp Arg His Met Glu Val Cys Tyr Ile Phe Ala Ser
                405                 410                 415

Glu Lys Lys Trp Ala Phe Ser Asp Glu Trp Val Ala Cys Leu Gly Ser
                420                 425                 430

Asn Arg Ala Leu Phe Arg Glu Pro Asp Leu Val Leu Arg Leu Leu Glu
            435                 440                 445

Thr Val Ile Asp Val Ser Thr Ala Asp Arg Ala Ile Pro Glu Ser Gln
    450                 455                 460

Ile Arg Gln Val Ile His Leu Ile Leu Glu Cys Tyr Ala Asp Leu Ser
465                 470                 475                 480

Leu Pro Gly Lys Asn Lys Val Leu Ala Gly Ile Leu Arg Ser Trp Gly
                485                 490                 495

Arg Lys Gly Leu Ser Glu Lys Leu Leu Ala Tyr Val Glu Gly Phe Gln
                500                 505                 510

Glu Asp Leu Asn Thr Thr Phe Asn Gln Leu Thr Gln Ser Ala Ser Glu
            515                 520                 525

Gln Gly Leu Ala Lys Ala Val Ala Ser Val Ala Arg Leu Val Ile Val
    530                 535                 540

His Pro Glu Val Thr Val Lys Lys Met Cys Ser Leu Ala Val Val Asn
545                 550                 555                 560

Leu Gly Thr His Lys Phe Leu Ala Gln Ile Leu Thr Ala Phe Pro Ala
                565                 570                 575

Leu Arg Phe Val Glu Val Gln Gly Pro Asn Ser Ser Ala Thr Phe Met
                580                 585                 590

Val Ser Cys Leu Lys Glu Thr Val Trp Met Lys Phe Ser Thr Pro Lys
            595                 600                 605

Glu Glu Lys Gln Phe Leu Glu Leu Leu Asn Cys Leu Met Ser Pro Val
    610                 615                 620

Lys Pro Gln Gly Ile Pro Val Ala Ala Leu Leu Glu Pro Asp Glu Val
625                 630                 635                 640

Leu Lys Glu Phe Val Leu Pro Phe Leu Arg Leu Asp Val Glu Glu Val
                645                 650                 655

Asp Leu Ser Leu Arg Ile Phe Ile Gln Thr Leu Glu Ala Asn Ala Cys
                660                 665                 670

Arg Glu Glu Tyr Trp Leu Gln Thr Cys Ser Pro Phe Pro Leu Leu Phe
            675                 680                 685

Ser Leu Cys Gln Leu Leu Asp Arg Phe Ser Lys Tyr Trp Gln Leu Pro
    690                 695                 700
```

-continued

Lys Glu Lys Arg Cys Leu Ser Leu Asp Arg Lys Asp Leu Ala Ile His
705                 710                 715                 720

Ile Leu Glu Leu Leu Cys Glu Ile Val Ser Ala Asn Ala Glu Thr Phe
                725                 730                 735

Ser Pro Asp Val Trp Ile Lys Ser Leu Ser Trp Leu His Arg Lys Leu
            740                 745                 750

Glu Gln Leu Asp Trp Thr Val Gly Leu Arg Leu Lys Ser Phe Phe Glu
        755                 760                 765

Gly His Phe Lys Cys Glu Val Pro Ala Thr Leu Phe Glu Ile Cys Lys
    770                 775                 780

Leu Ser Glu Asp Glu Trp Thr Ser Gln Ala His Pro Gly Tyr Gly Ala
785                 790                 795                 800

Gly Thr Gly Leu Leu Ala Trp Met Glu Cys Cys Val Ser Ser Gly
                805                 810                 815

Ile Ser Glu Arg Met Leu Ser Leu Leu Val Asp Val Gly Asn Pro
            820                 825                 830

Glu Glu Val Arg Leu Phe Ser Lys Gly Phe Leu Val Ala Leu Val Gln
        835                 840                 845

Val Met Pro Trp Cys Ser Pro Gln Glu Trp Gln Arg Leu His Gln Leu
    850                 855                 860

Thr Arg Arg Leu Leu Glu Lys Gln Leu Leu His Val Pro Tyr Ser Leu
865                 870                 875                 880

Glu Tyr Ile Gln Phe Val Pro Leu Leu Asn Leu Lys Pro Phe Ala Gln
                885                 890                 895

Glu Leu Gln Leu Ser Val Leu Phe Leu Arg Thr Phe Gln Phe Leu Cys
            900                 905                 910

Ser His Ser Cys Arg Asn Trp Leu Pro Leu Glu Gly Trp Asn His Val
        915                 920                 925

Val Lys Leu Leu Cys Gly Ser Leu Thr Arg Leu Leu Asp Ser Val Arg
    930                 935                 940

Ala Ile Gln Ala Ala Gly Pro Trp Val Gln Gly Pro Glu Gln Asp Leu
945                 950                 955                 960

Thr Gln Glu Ala Leu Phe Val Tyr Thr Gln Val Phe Cys His Ala Leu
                965                 970                 975

His Ile Met Ala Met Leu His Pro Glu Val Cys Glu Pro Leu Tyr Val
            980                 985                 990

Leu Ala Leu Glu Thr Leu Thr Cys Tyr Glu Thr Leu Ser Lys Thr Asn
        995                 1000                1005

Pro Ser Val Ser Ser Leu Leu Gln Arg Ala His Glu Gln Arg Phe
    1010                1015                1020

Leu Lys Ser Ile Ala Glu Gly Ile Gly Pro Glu Glu Arg Arg Gln
    1025                1030                1035

Thr Leu Leu Gln Lys Met Ser Ser Phe
    1040                1045

<210> SEQ ID NO 3
<211> LENGTH: 4750
<212> TYPE: DNA
<213> ORGANISM: Homo sapiens
<220> FEATURE:
<221> NAME/KEY: CDS
<222> LOCATION: (1341)..(4484)
<223> OTHER INFORMATION:

<400> SEQUENCE: 3
tggccgtgtg attgctctgt gcccattacc ctgtggccgt gtgactgctg ctgtgcccat    60

```
taccctgtgg ccgtgtgatt gctgctgtgc ccattaccct gtggccgtgt gattgctctg    120
tgcccattat cctgtggccg tgtgattgct ctgtgcccat accctgtgg ccgtgtgatt    180 gctctgtgcc cattaccctg tggccgtgtg attgctctgt gcccattatc ctgtggccgt    240
gtgattgctc tgtgcccatt atcctgtggc cgtgtgattg ctctgtgccc attatcctgt    300
ggccgtgtga ttgctctgtg cccattatcc tgtggccgtg tgattgctgc tgtgcccatt    360
accctgtggc cgtgtgattg ctctgtgccc attatcctgt ggccgtgtga ttgctctgtg    420
cccattatcc tgtggctgtg tgattgctct gtgcccatta cctgtagcc gtgtgattgc    480 ttctgtgccc attaccctgt ggctgtgtga ttgctgctgt gcccattatc ctgtggctgt    540
gtgattgctg ctgtgcccat accctgtggg ctgtgtgatg ctctgtgccc attaccctgt    600
ggctgtgtga ttgctctgtc ccattatcct gtggccgtgt gattgctgct gtgcctgtta    660
ccctgtggct gtgtgattgc tctgtgccca ttaccctgtg gctatgctcc cttcatctgt    720
catgagaagc tcagctgtca tgtcctgtgg tacatgctca gtggcccctg tagtttgtac    780
tgtcctccta tttctaaacc cctctcccca catcctctgc tggcccagcc tttgctggag    840
ggtctcgcct cagcagccca gcttttctt ttcacacact tttcctgaag atctcattc    900 accgtcttgg ttccggtgat cccctctggg cagataccctc tcagaatcac atttcccagc    960
ttacttccct cctgaacttc cacctggcat ttccgttgct ggaggacatc tgtaccttga   1020
tggccaaagc tgaactcatc tttcctcaca cctgctctga ttctcctcca ttccctgtat   1080
gtgatgtcac ctggtggcct cccagttccc aggctggaga gctcggaagc cattctggat   1140
tcctcggcca agtccttctg actccagctg tgcagtggct cttgtagtca tccattctcc   1200
ccgtccgctg atgtccttta aaacccttgt catctcaaac catgacagcc tactaacagc   1260
agtggccatc tggaaacatt ttcactatac tgtcttatt ggcttgtctg tgtgcaggac   1320
ccttgaacat ctgtgaagaa atg act att ctg cat gga ggc ttc ttg ctg gcc   1373
                     Met Thr Ile Leu His Gly Gly Phe Leu Leu Ala
                      1               5                  10 gag cag ctg ttc cac cct aag gca ctg gca gaa tta aca aag tct gac    1421
Glu Gln Leu Phe His Pro Lys Ala Leu Ala Glu Leu Thr Lys Ser Asp
           15                  20                  25 tgg gaa cgt gtt gga cgg ccc atc gtg gag gcc tta agg gag atc tcc    1469
Trp Glu Arg Val Gly Arg Pro Ile Val Glu Ala Leu Arg Glu Ile Ser
       30                  35                  40 tcg gct gca gca cac tcc cag ccc ttt gcc tgg aag aag aaa gcc ctg    1517
Ser Ala Ala His Ser Gln Pro Phe Ala Trp Lys Lys Lys Ala Leu
   45                  50                  55 atc atc atc tgg gcc aag gtt ctg cag ccg cac ccc gtg acc ccg tcc    1565
Ile Ile Ile Trp Ala Lys Val Leu Gln Pro His Pro Val Thr Pro Ser
60                  65                  70                  75 gac aca gag aca cgg tgg cag gaa gac ctg ttc ttc tcg gtg ggc aac    1613
Asp Thr Glu Thr Arg Trp Gln Glu Asp Leu Phe Phe Ser Val Gly Asn
               80                  85                  90 atg atc ccc acc atc aac cac acc atc ctc ttc gag ctg ctc aaa tcc    1661
Met Ile Pro Thr Ile Asn His Thr Ile Leu Phe Glu Leu Leu Lys Ser
           95                 100                 105 ctg gaa gct tct gga ctc ttt atc cag ctc ctg atg gcc ctg ccc acc    1709
Leu Glu Ala Ser Gly Leu Phe Ile Gln Leu Leu Met Ala Leu Pro Thr
       110                 115                 120 acc atc tgc cat gca gaa cta gag cgc ttt ctg gaa cat gtg acc gtt    1757
Thr Ile Cys His Ala Glu Leu Glu Arg Phe Leu Glu His Val Thr Val
   125                 130                 135
```

```
                                                           -continued
gac act tct gcc gaa gac gtg gcc ttc ttc ctg gac gtc tgg tgg gag           1805
Asp Thr Ser Ala Glu Asp Val Ala Phe Phe Leu Asp Val Trp Trp Glu
140                 145                 150                 155 gtg atg aag cac aag ggt cac ccg cag gac ccc ctg ctc tcc cag ttt           1853
Val Met Lys His Lys Gly His Pro Gln Asp Pro Leu Leu Ser Gln Phe
                160                 165                 170 agt gca atg gcc cat aag tac ctg cct gcc tta gat gag ttc ccc cat           1901
Ser Ala Met Ala His Lys Tyr Leu Pro Ala Leu Asp Glu Phe Pro His
            175                 180                 185 cct cca aag agg ctt agg tca gac cca gac gcg tgc ccc acc atg ccc           1949
Pro Pro Lys Arg Leu Arg Ser Asp Pro Asp Ala Cys Pro Thr Met Pro
        190                 195                 200 ctg ttg gcc atg ctg ctc cgc ggg ctg aca cag atc cag agt cgg atc           1997
Leu Leu Ala Met Leu Leu Arg Gly Leu Thr Gln Ile Gln Ser Arg Ile
205                 210                 215 ctg ggc ccg ggg agg aag tgc tgt gcg ctg gcc aac ctg gct gac atg           2045
Leu Gly Pro Gly Arg Lys Cys Cys Ala Leu Ala Asn Leu Ala Asp Met
220                 225                 230                 235 ctg act gtg ttt gcg ctg aca gag gac gac ccc cag gag gtg tct gca           2093
Leu Thr Val Phe Ala Leu Thr Glu Asp Asp Pro Gln Glu Val Ser Ala
                240                 245                 250 acc gtg tat ctg gac aaa ctg gcc acg gtg atc tct gtg tgg aac tcg           2141
Thr Val Tyr Leu Asp Lys Leu Ala Thr Val Ile Ser Val Trp Asn Ser
            255                 260                 265 gac acc cag aat ccc tac cac cag cag gcg ctg gca gag aag gtg aag           2189
Asp Thr Gln Asn Pro Tyr His Gln Gln Ala Leu Ala Glu Lys Val Lys
        270                 275                 280 gag gca gaa cgg gat gtc agc ctg acc tcg ctg gcc aaa ctc ccc agt           2237
Glu Ala Glu Arg Asp Val Ser Leu Thr Ser Leu Ala Lys Leu Pro Ser
285                 290                 295 gag acc att ttc gtg ggc tgc gag ttc ctg cac cac ctg ctg cgg gag           2285
Glu Thr Ile Phe Val Gly Cys Glu Phe Leu His His Leu Leu Arg Glu
300                 305                 310                 315 tgg ggg gag gag ttg cag gcc gtg ctc cgc agc agc cag ggg aca agt           2333
Trp Gly Glu Glu Leu Gln Ala Val Leu Arg Ser Ser Gln Gly Thr Ser
                320                 325                 330 tac gac agc tac cgg ctg tgc gac agt ctg act tcc ttc agc cag aac           2381
Tyr Asp Ser Tyr Arg Leu Cys Asp Ser Leu Thr Ser Phe Ser Gln Asn
            335                 340                 345 gcg acg ctc tac ctg aac cgc acc agc ctg tcc aag gag gac agg cag           2429
Ala Thr Leu Tyr Leu Asn Arg Thr Ser Leu Ser Lys Glu Asp Arg Gln
        350                 355                 360 gtg gtc tct gag ctg gcg gag tgt gtc agg gac ttc ctg agg aaa acg           2477
Val Val Ser Glu Leu Ala Glu Cys Val Arg Asp Phe Leu Arg Lys Thr
365                 370                 375 agc acg gtg ctg aag aac agg gcc ttg gag gat atc aca gct tcc att           2525
Ser Thr Val Leu Lys Asn Arg Ala Leu Glu Asp Ile Thr Ala Ser Ile
380                 385                 390                 395 gcc atg gcc gtc atc cag cag aag atg gac cgc cat atg gaa gtg tgc           2573
Ala Met Ala Val Ile Gln Gln Lys Met Asp Arg His Met Glu Val Cys
                400                 405                 410 tac att ttt gcc tct gag aag aag tgg gcc ttc tcg gac gag tgg gta           2621
Tyr Ile Phe Ala Ser Glu Lys Lys Trp Ala Phe Ser Asp Glu Trp Val
            415                 420                 425 gcc tgc ctg ggg agt aac agg gcc ctc ttc cga gag cca gac ttg gtg           2669
Ala Cys Leu Gly Ser Asn Arg Ala Leu Phe Arg Glu Pro Asp Leu Val
        430                 435                 440 ttg agg ctg ctg gaa aca gtg ata gac gtc agc aca gct gac aga gcc           2717
Leu Arg Leu Leu Glu Thr Val Ile Asp Val Ser Thr Ala Asp Arg Ala
445                 450                 455
```

-continued

| | |
|---|---|
| atc cct gag tct cag atc cgg cag gtg atc cac ctg atc ctg gaa tgt<br>Ile Pro Glu Ser Gln Ile Arg Gln Val Ile His Leu Ile Leu Glu Cys<br>460                        465                  470                475 | 2765 |
| tac gca gac ctc tcc ctg cca ggt aaa aat aaa gtc ctt gca ggt atc<br>Tyr Ala Asp Leu Ser Leu Pro Gly Lys Asn Lys Val Leu Ala Gly Ile<br>                      480                    485                  490 | 2813 |
| ctg cgt tcc tgg ggg cga aag ggc ctc tct gaa aag ttg ctg gct tat<br>Leu Arg Ser Trp Gly Arg Lys Gly Leu Ser Glu Lys Leu Leu Ala Tyr<br>              495                  500                  505 | 2861 |
| gtg gag ggt ttt cag gaa gac ctc aat aca act ttt aac cag ctc act<br>Val Glu Gly Phe Gln Glu Asp Leu Asn Thr Thr Phe Asn Gln Leu Thr<br>510                        515                  520 | 2909 |
| cag agt gcc tcc gaa cag ggc ttg gca aaa gct gtg gcc tcc gtg gcc<br>Gln Ser Ala Ser Glu Gln Gly Leu Ala Lys Ala Val Ala Ser Val Ala<br>525                        530                  535 | 2957 |
| cgc ctg gtc ata gtg cac ccg gaa gtc acg gtg aag aaa atg tgc agc<br>Arg Leu Val Ile Val His Pro Glu Val Thr Val Lys Lys Met Cys Ser<br>540                        545                  550                555 | 3005 |
| ctg gct gtg gtc aat ctc ggc acc cac aag ttc ctg gcc cag att ctc<br>Leu Ala Val Val Asn Leu Gly Thr His Lys Phe Leu Ala Gln Ile Leu<br>                      560                  565                  570 | 3053 |
| act gcc ttc gct gcc ctt agg ttt gtg gaa gag cag ggt ccc aat tca<br>Thr Ala Phe Ala Ala Leu Arg Phe Val Glu Glu Gln Gly Pro Asn Ser<br>              575                  580                  585 | 3101 |
| tct gcc act ttc atg gtg tca tgc ctc aaa gaa acc gtc tgg atg aag<br>Ser Ala Thr Phe Met Val Ser Cys Leu Lys Glu Thr Val Trp Met Lys<br>                      590                  595                  600 | 3149 |
| ttc tct aca ccc aag gaa gaa aag caa ttt tta gag ctc ctg aac tgc<br>Phe Ser Thr Pro Lys Glu Glu Lys Gln Phe Leu Glu Leu Leu Asn Cys<br>605                        610                  615 | 3197 |
| ctg atg agt ccc gtg aaa ccc caa ggg att cca gtg gct gct ctt ctt<br>Leu Met Ser Pro Val Lys Pro Gln Gly Ile Pro Val Ala Ala Leu Leu<br>620                        625                  630                635 | 3245 |
| gag cca gac gag gtg ctg aag gaa ttt gtc ctg cct ttc ttg agg tta<br>Glu Pro Asp Glu Val Leu Lys Glu Phe Val Leu Pro Phe Leu Arg Leu<br>                      640                    645                  650 | 3293 |
| gat gtt gaa gag gta gac ctc agt ctg agg atc ttc atc cag act cta<br>Asp Val Glu Glu Val Asp Leu Ser Leu Arg Ile Phe Ile Gln Thr Leu<br>              655                  660                  665 | 3341 |
| gag gca aac gcg tgt cga gag gaa tac tgg ctc cag acc tgc tcc ccg<br>Glu Ala Asn Ala Cys Arg Glu Glu Tyr Trp Leu Gln Thr Cys Ser Pro<br>                      670                    675                  680 | 3389 |
| ttt cca ctc ctc ttc agc ttg tgc cag ctc ttg gac cgc ttc agc aaa<br>Phe Pro Leu Leu Phe Ser Leu Cys Gln Leu Leu Asp Arg Phe Ser Lys<br>685                        690                  695 | 3437 |
| tac tgg cag ctt ccc aag gag aag cgg tgc ctc tct ttg gat agg aag<br>Tyr Trp Gln Leu Pro Lys Glu Lys Arg Cys Leu Ser Leu Asp Arg Lys<br>700                        705                  710                715 | 3485 |
| gat cta gcg atc cat atc ctg gag ctc ctg tgt gag att gta tca gcc<br>Asp Leu Ala Ile His Ile Leu Glu Leu Leu Cys Glu Ile Val Ser Ala<br>                      720                    725                  730 | 3533 |
| aat gct gag acc ttc tcc ccg gat gtc tgg atc aag tcc ctg tcc tgg<br>Asn Ala Glu Thr Phe Ser Pro Asp Val Trp Ile Lys Ser Leu Ser Trp<br>              735                  740                  745 | 3581 |
| ctc cac cgc aag tta gaa cag cta gac tgg act gtg ggc ctg agg ctg<br>Leu His Arg Lys Leu Glu Gln Leu Asp Trp Thr Val Gly Leu Arg Leu<br>750                        755                  760 | 3629 |
| aag agc ttc ttc gag ggg cac ttc aag tgt gaa gtg cca gcc aca ctt<br>Lys Ser Phe Phe Glu Gly His Phe Lys Cys Glu Val Pro Ala Thr Leu | 3677 |

-continued

| | | |
|---|---|---|
| ttt gag atc tgt aag ctt tca gaa gac gag tgg acc tcc cag gcc cac<br>Phe Glu Ile Cys Lys Leu Ser Glu Asp Glu Trp Thr Ser Gln Ala His<br>780                        785                        790                        795 | 3725 |
| cca ggg tac ggg gct ggc acg ggg ctc ctg gcc tgg atg gag tgc tgc<br>Pro Gly Tyr Gly Ala Gly Thr Gly Leu Leu Ala Trp Met Glu Cys Cys<br>800                              805                            810 | 3773 |
| tgc gtc tcc agc ggc atc tcg gag agg atg ctg tct ctc ttg gtg gtg<br>Cys Val Ser Ser Gly Ile Ser Glu Arg Met Leu Ser Leu Leu Val Val<br>        815                        820                        825 | 3821 |
| gac gtg ggc aat cct gag gag gtc aga ctg ttc agc aaa ggc ttt ctg<br>Asp Val Gly Asn Pro Glu Glu Val Arg Leu Phe Ser Lys Gly Phe Leu<br>830                        835                        840 | 3869 |
| gtg gcc ctg gtg caa gtc atg cct tgg tgc agc cct cag gag tgg cag<br>Val Ala Leu Val Gln Val Met Pro Trp Cys Ser Pro Gln Glu Trp Gln<br>845                        850                        855 | 3917 |
| cgc ctt cac cag ctg acc agg aga ctg ctg gag aag cag ctc ctc cat<br>Arg Leu His Gln Leu Thr Arg Arg Leu Leu Glu Lys Gln Leu Leu His<br>860                        865                        870                        875 | 3965 |
| gtc cct tat agc ctg gaa tat att cag ttt gtt ccc ctg ctc aac ctg<br>Val Pro Tyr Ser Leu Glu Tyr Ile Gln Phe Val Pro Leu Leu Asn Leu<br>        880                        885                        890 | 4013 |
| aag ccc ttt gcc cag gag ttg caa ctc tcc gtc ctc ttc ctg agg act<br>Lys Pro Phe Ala Gln Glu Leu Gln Leu Ser Val Leu Phe Leu Arg Thr<br>895                        900                        905 | 4061 |
| ttc cag ttt ctc tgc agc cat agc tgt cgt aat tgg ctt cct ctg gaa<br>Phe Gln Phe Leu Cys Ser His Ser Cys Arg Asn Trp Leu Pro Leu Glu<br>910                        915                        920 | 4109 |
| ggc tgg aac cac gtg gtc aaa ctc ctc tgt ggc agt ctg acc cgc ctc<br>Gly Trp Asn His Val Val Lys Leu Leu Cys Gly Ser Leu Thr Arg Leu<br>925                        930                        935 | 4157 |
| ctg gac tca gtc agg gcg ata cag gca gct ggc cct tgg gtt caa gga<br>Leu Asp Ser Val Arg Ala Ile Gln Ala Ala Gly Pro Trp Val Gln Gly<br>940                        945                        950                        955 | 4205 |
| cca gag cag gac ctg acc cag gaa gcc ctg ttt gtt tac acc cag gtg<br>Pro Glu Gln Asp Leu Thr Gln Glu Ala Leu Phe Val Tyr Thr Gln Val<br>                  960                        965                        970 | 4253 |
| ttc tgc cat gct ctg cac atc atg gcc atg ctc cac ccg gag gtc tgt<br>Phe Cys His Ala Leu His Ile Met Ala Met Leu His Pro Glu Val Cys<br>975                        980                        985 | 4301 |
| gag cca ctc tac gtt tta gcc ttg gaa acc ctc acc tgc  tat gag act<br>Glu Pro Leu Tyr Val Leu Ala Leu Glu Thr Leu Thr Cys  Tyr Glu Thr<br>990                        995                        1000 | 4349 |
| ttg agc  aag acc aac cct tct  gtc agc tcc ttg ctc  cag agg gca<br>Leu Ser  Lys Thr Asn Pro Ser  Val Ser Ser Leu Leu  Gln Arg Ala<br>1005                        1010                      1015 | 4394 |
| cac gag  cag tgc ttc tta aag  tcc att gct gag ggc  att ggc cct<br>His Glu  Gln Cys Phe Leu Lys  Ser Ile Ala Glu Gly  Ile Gly Pro<br>1020                        1025                      1030 | 4439 |
| gaa gaa  cgg cgc caa acc ctg  ttg cag aag atg agc  agc ttc tga<br>Glu Glu  Arg Arg Gln Thr Leu  Leu Gln Lys Met Ser  Ser Phe<br>1035                        1040                      1045 | 4484 |
| cttggcgtgg ggagctgggc cccaacatgg cgggtctgca aagatcagc agcttcttac | 4544 |
| ctgtgcggga gcgaaaaagc tgggcttcaa catggcaggt ctgtaggggt cagacccgag | 4604 |
| cagcctggac tttacagtta tgtgaaactg tccacaaaaa gtcatggcaa taatggtgta | 4664 |
| aagaaaatag tttcttgggt atttgtaacg tacaaactat cataaaaatt ctcctctttc | 4724 |
| ccaaaaaaaa aaaaaaaaa aaaaaa | 4750 |

<210> SEQ ID NO 4
<211> LENGTH: 1047
<212> TYPE: PRT
<213> ORGANISM: Homo sapiens

<400> SEQUENCE: 4

```
Met Thr Ile Leu His Gly Gly Phe Leu Leu Ala Glu Gln Leu Phe His
1               5                   10                  15

Pro Lys Ala Leu Ala Glu Leu Thr Lys Ser Asp Trp Glu Arg Val Gly
            20                  25                  30

Arg Pro Ile Val Glu Ala Leu Arg Glu Ile Ser Ser Ala Ala Ala His
        35                  40                  45

Ser Gln Pro Phe Ala Trp Lys Lys Ala Leu Ile Ile Ile Trp Ala
    50                  55                  60

Lys Val Leu Gln Pro His Pro Val Thr Pro Ser Asp Thr Glu Thr Arg
65                  70                  75                  80

Trp Gln Glu Asp Leu Phe Ser Val Gly Asn Met Ile Pro Thr Ile
                85                  90                  95

Asn His Thr Ile Leu Phe Glu Leu Leu Lys Ser Leu Glu Ala Ser Gly
            100                 105                 110

Leu Phe Ile Gln Leu Leu Met Ala Leu Pro Thr Thr Ile Cys His Ala
        115                 120                 125

Glu Leu Glu Arg Phe Leu Glu His Val Thr Val Asp Thr Ser Ala Glu
    130                 135                 140

Asp Val Ala Phe Phe Leu Asp Val Trp Trp Glu Val Met Lys His Lys
145                 150                 155                 160

Gly His Pro Gln Asp Pro Leu Leu Ser Gln Phe Ser Ala Met Ala His
                165                 170                 175

Lys Tyr Leu Pro Ala Leu Asp Glu Phe Pro His Pro Pro Lys Arg Leu
            180                 185                 190

Arg Ser Asp Pro Asp Ala Cys Pro Thr Met Pro Leu Leu Ala Met Leu
        195                 200                 205

Leu Arg Gly Leu Thr Gln Ile Gln Ser Arg Ile Leu Gly Pro Gly Arg
    210                 215                 220

Lys Cys Cys Ala Leu Ala Asn Leu Ala Asp Met Leu Thr Val Phe Ala
225                 230                 235                 240

Leu Thr Glu Asp Asp Pro Gln Glu Val Ser Ala Thr Val Tyr Leu Asp
                245                 250                 255

Lys Leu Ala Thr Val Ile Ser Val Trp Asn Ser Asp Thr Gln Asn Pro
            260                 265                 270

Tyr His Gln Gln Ala Leu Ala Glu Lys Val Lys Glu Ala Glu Arg Asp
        275                 280                 285

Val Ser Leu Thr Ser Leu Ala Lys Leu Pro Ser Glu Thr Ile Phe Val
    290                 295                 300

Gly Cys Glu Phe Leu His His Leu Leu Arg Glu Trp Gly Glu Glu Leu
305                 310                 315                 320

Gln Ala Val Leu Arg Ser Ser Gln Gly Thr Ser Tyr Asp Ser Tyr Arg
                325                 330                 335

Leu Cys Asp Ser Leu Thr Ser Phe Ser Gln Asn Ala Thr Leu Tyr Leu
            340                 345                 350

Asn Arg Thr Ser Leu Ser Lys Glu Asp Arg Gln Val Val Ser Glu Leu
        355                 360                 365

Ala Glu Cys Val Arg Asp Phe Leu Arg Lys Thr Ser Thr Val Leu Lys
```

```
                370             375             380
Asn Arg Ala Leu Glu Asp Ile Thr Ala Ser Ile Ala Met Ala Val Ile
385                 390                 395                 400

Gln Gln Lys Met Asp Arg His Met Glu Val Cys Tyr Ile Phe Ala Ser
                405                 410                 415

Glu Lys Lys Trp Ala Phe Ser Asp Glu Trp Val Ala Cys Leu Gly Ser
                420                 425                 430

Asn Arg Ala Leu Phe Arg Glu Pro Asp Leu Val Leu Arg Leu Leu Glu
            435                 440                 445

Thr Val Ile Asp Val Ser Thr Ala Asp Arg Ala Ile Pro Glu Ser Gln
450                 455                 460

Ile Arg Gln Val Ile His Leu Ile Leu Glu Cys Tyr Ala Asp Leu Ser
465                 470                 475                 480

Leu Pro Gly Lys Asn Lys Val Leu Ala Gly Ile Leu Arg Ser Trp Gly
                485                 490                 495

Arg Lys Gly Leu Ser Glu Lys Leu Leu Ala Tyr Val Glu Gly Phe Gln
                500                 505                 510

Glu Asp Leu Asn Thr Thr Phe Asn Gln Leu Thr Gln Ser Ala Ser Glu
            515                 520                 525

Gln Gly Leu Ala Lys Ala Val Ala Ser Val Ala Arg Leu Val Ile Val
530                 535                 540

His Pro Glu Val Thr Val Lys Lys Met Cys Ser Leu Ala Val Val Asn
545                 550                 555                 560

Leu Gly Thr His Lys Phe Leu Ala Gln Ile Leu Thr Ala Phe Ala Ala
                565                 570                 575

Leu Arg Phe Val Glu Glu Gln Gly Pro Asn Ser Ser Ala Thr Phe Met
            580                 585                 590

Val Ser Cys Leu Lys Glu Thr Val Trp Met Lys Phe Ser Thr Pro Lys
            595                 600                 605

Glu Glu Lys Gln Phe Leu Glu Leu Leu Asn Cys Leu Met Ser Pro Val
            610                 615                 620

Lys Pro Gln Gly Ile Pro Val Ala Ala Leu Leu Glu Pro Asp Glu Val
625                 630                 635                 640

Leu Lys Glu Phe Val Leu Pro Phe Leu Arg Leu Asp Val Glu Glu Val
                645                 650                 655

Asp Leu Ser Leu Arg Ile Phe Ile Gln Thr Leu Glu Ala Asn Ala Cys
            660                 665                 670

Arg Glu Glu Tyr Trp Leu Gln Thr Cys Ser Pro Phe Pro Leu Leu Phe
            675                 680                 685

Ser Leu Cys Gln Leu Leu Asp Arg Phe Ser Lys Tyr Trp Gln Leu Pro
690                 695                 700

Lys Glu Lys Arg Cys Leu Ser Leu Asp Arg Lys Asp Leu Ala Ile His
705                 710                 715                 720

Ile Leu Glu Leu Leu Cys Glu Ile Val Ser Ala Asn Ala Glu Thr Phe
                725                 730                 735

Ser Pro Asp Val Trp Ile Lys Ser Leu Ser Trp Leu His Arg Lys Leu
            740                 745                 750

Glu Gln Leu Asp Trp Thr Val Gly Leu Arg Leu Lys Ser Phe Phe Glu
            755                 760                 765

Gly His Phe Lys Cys Glu Val Pro Ala Thr Leu Phe Glu Ile Cys Lys
            770                 775                 780

Leu Ser Glu Asp Glu Trp Thr Ser Gln Ala His Pro Gly Tyr Gly Ala
785                 790                 795                 800
```

Gly Thr Gly Leu Leu Ala Trp Met Glu Cys Cys Cys Val Ser Ser Gly
            805                 810                 815

Ile Ser Glu Arg Met Leu Ser Leu Leu Val Val Asp Val Gly Asn Pro
            820                 825                 830

Glu Glu Val Arg Leu Phe Ser Lys Gly Phe Leu Val Ala Leu Val Gln
            835                 840                 845

Val Met Pro Trp Cys Ser Pro Gln Glu Trp Gln Arg Leu His Gln Leu
            850                 855                 860

Thr Arg Arg Leu Leu Glu Lys Gln Leu Leu His Val Pro Tyr Ser Leu
865                 870                 875                 880

Glu Tyr Ile Gln Phe Val Pro Leu Leu Asn Leu Lys Pro Phe Ala Gln
                885                 890                 895

Glu Leu Gln Leu Ser Val Leu Phe Leu Arg Thr Phe Gln Phe Leu Cys
                900                 905                 910

Ser His Ser Cys Arg Asn Trp Leu Pro Leu Glu Gly Trp Asn His Val
            915                 920                 925

Val Lys Leu Leu Cys Gly Ser Leu Thr Arg Leu Leu Asp Ser Val Arg
930                 935                 940

Ala Ile Gln Ala Ala Gly Pro Trp Val Gln Gly Pro Glu Gln Asp Leu
945                 950                 955                 960

Thr Gln Glu Ala Leu Phe Val Tyr Thr Gln Val Phe Cys His Ala Leu
                965                 970                 975

His Ile Met Ala Met Leu His Pro Glu Val Cys Glu Pro Leu Tyr Val
            980                 985                 990

Leu Ala Leu Glu Thr Leu Thr Cys  Tyr Glu Thr Leu Ser  Lys Thr Asn
        995                 1000                1005

Pro Ser  Val Ser Ser Leu Leu  Gln Arg Ala His Glu  Gln Cys Phe
    1010                1015                1020

Leu Lys  Ser Ile Ala Glu Gly  Ile Gly Pro Glu Glu  Arg Arg Gln
    1025                1030                1035

Thr Leu  Leu Gln Lys Met Ser  Ser Phe
    1040                1045

<210> SEQ ID NO 5
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: primer

<400> SEQUENCE: 5
ctgcccacca ccatctgcca                                              20

<210> SEQ ID NO 6
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: primer

<400> SEQUENCE: 6
agcagcatgg ccaacagggg                                              20

<210> SEQ ID NO 7

```
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: primer

<400> SEQUENCE: 7
tgtggagggt tttcaggaag                                              20

<210> SEQ ID NO 8
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: primer

<400> SEQUENCE: 8
tggagccagt attcctctcg                                              20
```